United States Patent [19]

Ikewaki et al.

[11] Patent Number: 5,677,150

[45] Date of Patent: Oct. 14, 1997

[54] ANTIBODIES PRODUCED FROM LIPOPOLYSACCHARIDE-STIMULATED MONOCYTE/MACPROPHAGE CELL LINES

[75] Inventors: Nobunao Ikewaki, Sagamihara; Hidetoshi Inoko, Atsugi, both of Japan

[73] Assignee: Fujisawa Pharmaceutical Co., Ltd., Osaka, Japan

[21] Appl. No.: 603,090

[22] Filed: Feb. 20, 1996

Related U.S. Application Data

[63] Continuation of Ser. No. 143,068, Oct. 29, 1993, abandoned.

[30] Foreign Application Priority Data

Nov. 26, 1992 [JP] Japan .................................. 4-341228
Mar. 18, 1993 [JP] Japan .................................. 5-085537

[51] Int. Cl.$^6$ .............................. C12P 21/08; C12N 5/12; C07K 16/18
[52] U.S. Cl. .................... 435/70.21; 438/172.2; 438/240.27; 530/388.7; 530/388.73; 530/388.75; 530/388.4
[58] Field of Search ................ 530/388.7, 388.73, 530/388.75, 388.4; 435/240.27, 172.2, 70.21

[56] References Cited

PUBLICATIONS

Harris et al., Tibtech, 11:42–44, 1993.
W. Waldmann et al., Immunology Today, 14(6):247–251, 1993.
I. Kawaki et al., Jpn. J. Bacteriol, 48(2):429–433, 1993.
Waldmann, T., Science, 252:1657–1662, 21 Jun. 1991.
Proceedings of Japanese Society for Immunology, vol. 22, Oct. 30, 1992, p. 258, along with translation (3 pages).
Davignon, Denise et al., J. Immunol, 127(2):590–595, 1981.

Primary Examiner—James C. Housel
Assistant Examiner—Susan A. Loring
Attorney, Agent, or Firm—Oblon, Spivak, McClelland, Maier & Neustadt, P.C.

[57] ABSTRACT

Lipopolysaccharide-stimulated monocyte/macrophage cell lines are used as antigens to obtain antibodies. Antibodies which inhibit intercellular adhesion of cells stimulated by a differentiation factor or which induce intercellular aggregation of cells in the process of differentiation under stimulation by a differentiation factor are disclosed. Such antibodies can be used to suppress immune responses and in clinical diagnosis of immune system disorders.

15 Claims, 17 Drawing Sheets

U937 alone

U937+NMS(15μg)

U937+NI-11(15μg)

U937+TOK-45(15μg)

LPS-U937 alone

LPS-U937+NMS

LPS-U937+NI-11

LPS-U937+TOK-45

LPS-U937+NI-11(15μg)

LPS-U937+NI-11+
anti-CD18(L130)(25μg)

LPS-U937+NI-11+
anti-CD54(LB-2)(25μg)

LPS-U937+NI-11+
anti-CD58(L306.4)(25μg)

LPS-U937+NI-11(15μg)

LPS-U937+NI-11+SPHINGOSINE(2μM)

LPS-U937+NI-11+ H-7(2μM)

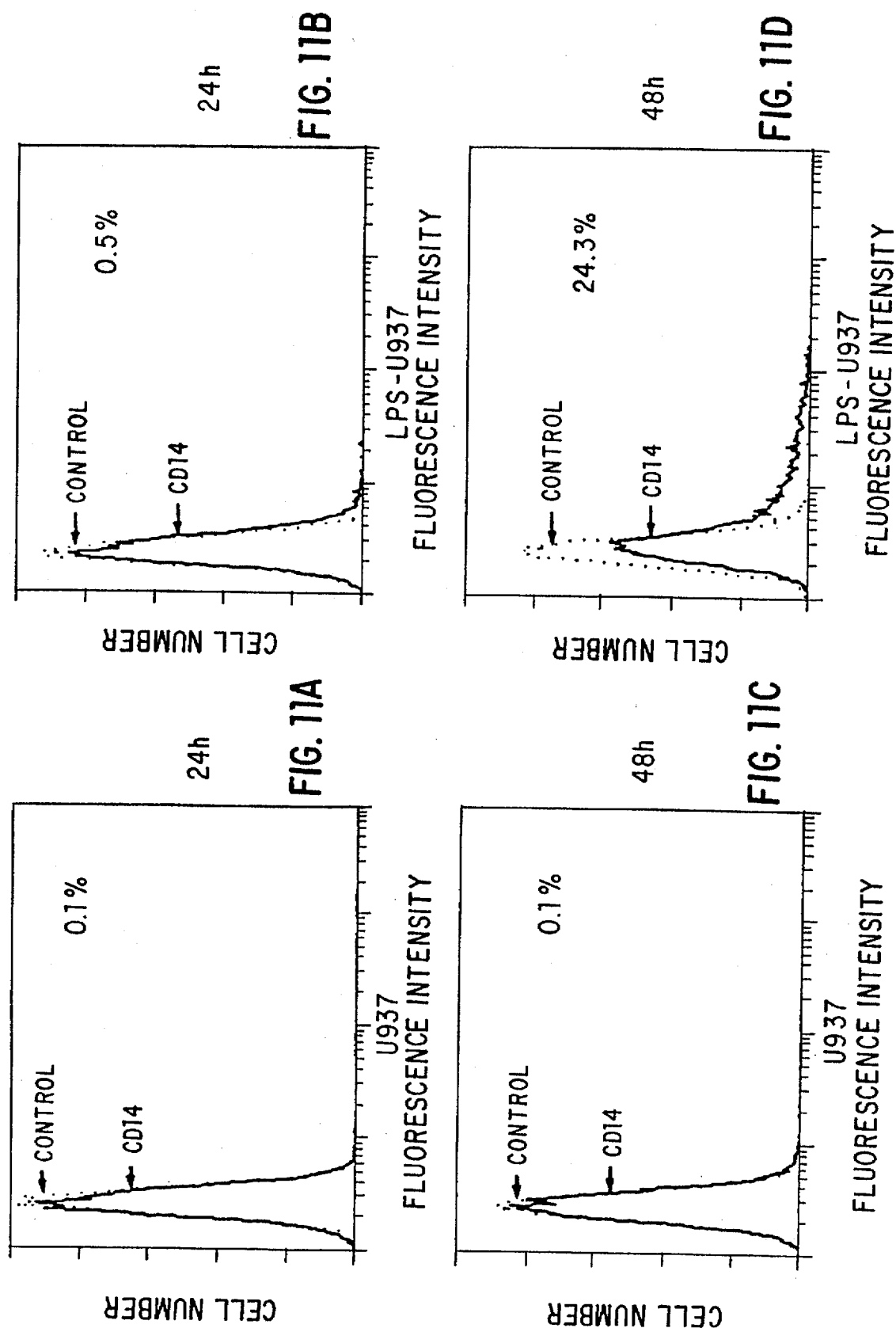

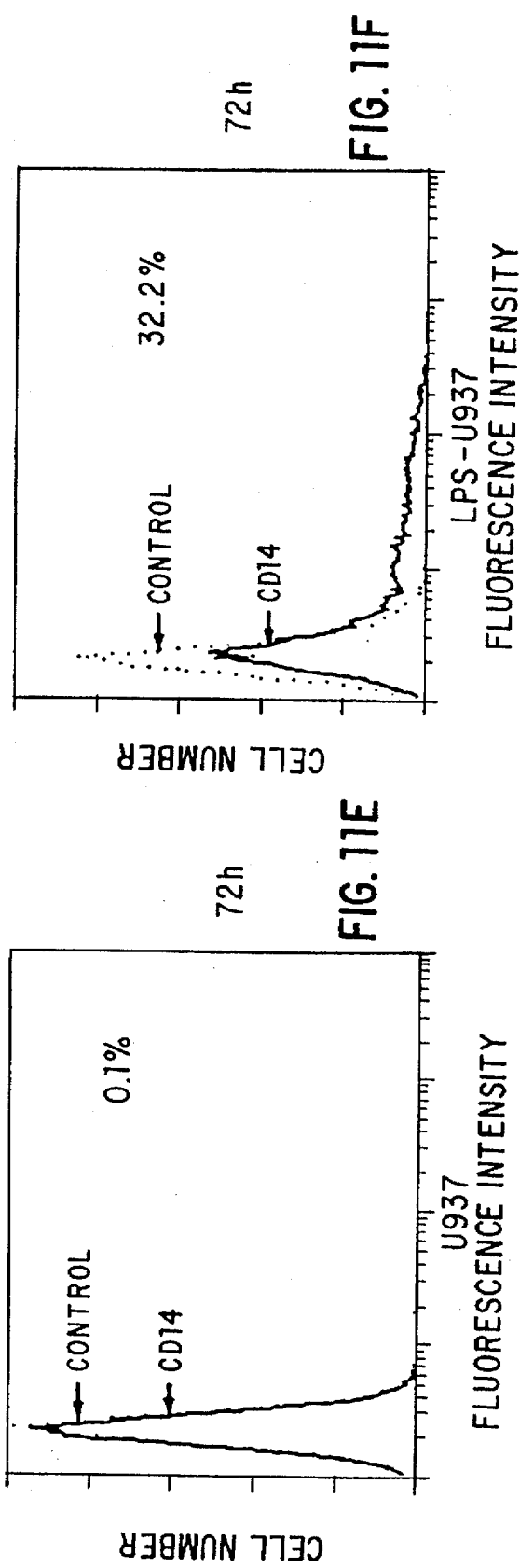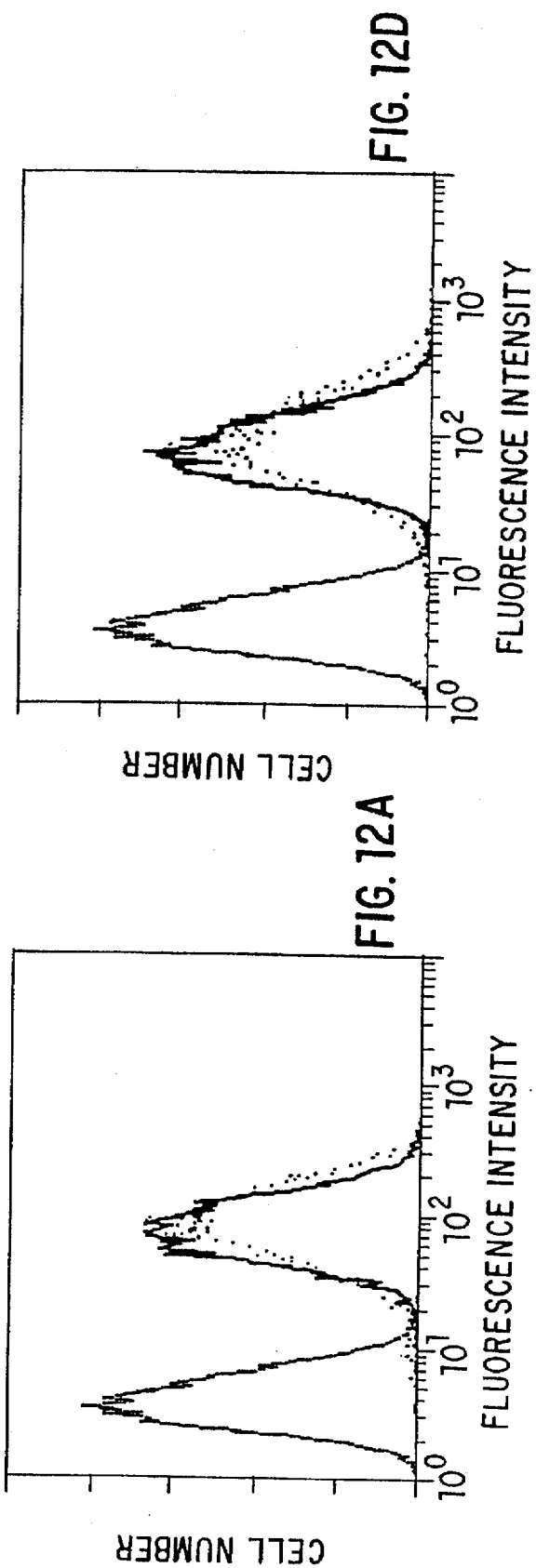

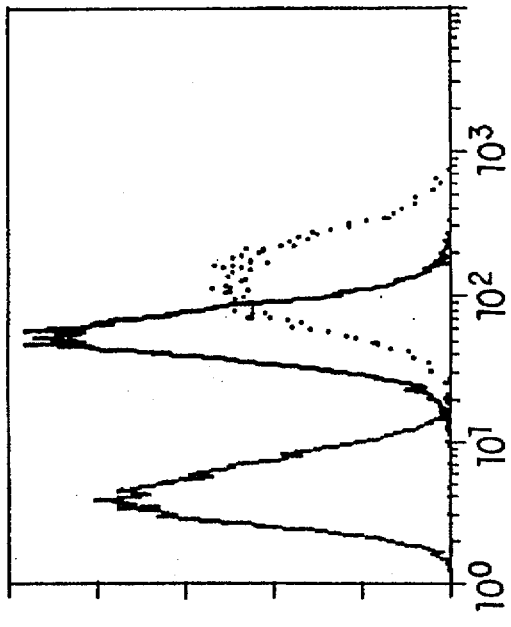
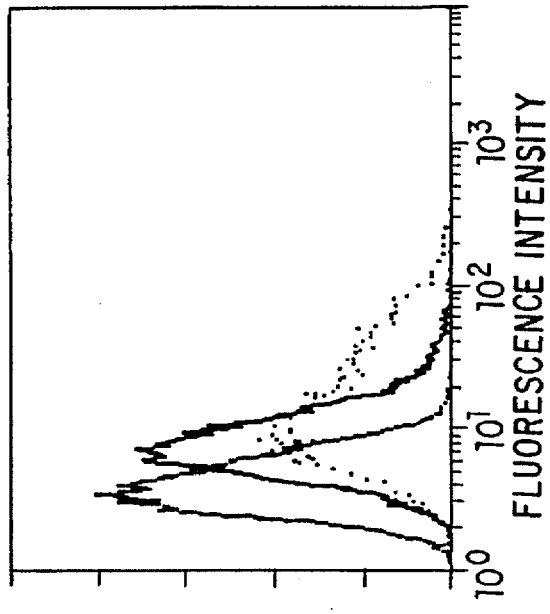
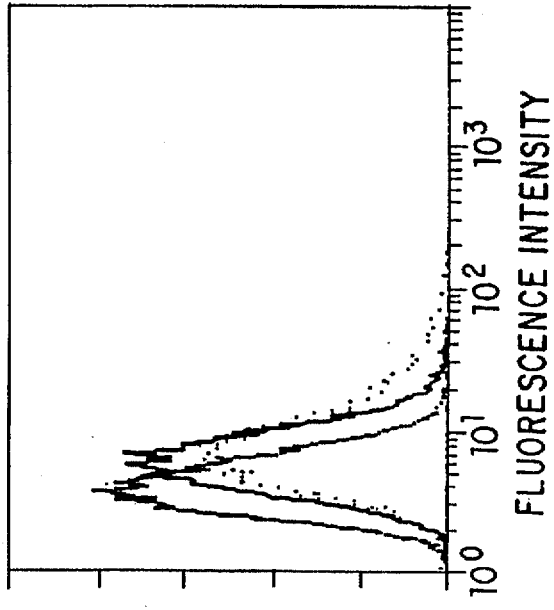

ANTIBODIES PRODUCED FROM LIPOPOLYSACCHARIDE-STIMULATED MONOCYTE/MACPROPHAGE CELL LINES

This application is a continuation of application Ser. No. 08/143,068, filed on Oct. 29, 1993, now abandoned.

This invention relates to antibodies obtainable by using a lipopolysaccharide-stimulated monocyte/macrophage cell line as an antigen and a method for producing the antibodies, and finds application in the field of medicine.

While various organs form in the process of organogenesis and cells multiply in line with growth to form cell aggregates, it is the adhesion molecules that is indispensable to the formation of such aggregates.

The adhesion molecules are not only involved in cell-to-cell binding but also take charge of the exchange of information between cells to mediate the intercellular information network and thereby control the homeostasis of the whole body.

Today, the adhesion molecules are generally divided into several families according to their structures and it is known that various types of adhesion molecules are selectively put to use according to various physiological conditions. For example, LFA-2 (CD2), CD4, CD8 and CD54 on the T-cell can be classified into the Ig super-family, while LFA-1 (CD11a/CD18, CD11b/CD18, CD11c/CD18) which is omnipresent on the leukocytes can be classified into the integrin family. It is, thus, considered that adhesion molecules mediate the intracellular information network to control the immune system of the host body. Thus, adhesion molecules in a sense play an important role in the induction of physiological defense mechanisms and are probably associated, in a significant measure, with defense against infection due to the inroad of adventitious microorganisms.

For example, while a variety of cell groups are involved in defense against infection of the body, the monocyte/macrophage series cells are associated with initial defense. On the other hand, it appears that after establishment of defense, homotypic cell aggregation (hereinafer referred to sometimes as HCA) due to various cytokines, namely intercellular adhesion, occurs to take charge of the transmission of information between cells. Particularly in infections with gram-negative bacteria, it is conjectured that lipopolysaccharide (hereinafter referred to sometimes as LPS) which is a constituent of the microorganism and a potent inducer of various cytokines plays a dominant role. Thus, LPS is suspected to be controlling the expression of certain adhesion molecules on the surface of monocyte/macrophage cells. However, there has not known to this day an antibody obtainable by using an LPS-stimulated monocyte/macrophage cell line as the antigen.

It is known that among the adhesion molecules mentioned above, LFA-1 (lymphocyte function-associated antigen-1)-ICAM-1 (intercellular adhesion molecule-1, CD54) in particular plays an important role in various interactions of the immune system, such as adhesion of leukocytes to vascular endothelial cells and the antigen-specific reactions of lymphocytes, among others.

Inhibiting the interadhesion of cells is useful for suppressing immune reactions, such as suppression of graft rejection following organ transplantation.

As monoclonal antibodies which inhibit such intercellular adhesion, LB-2, a monoclonal antibody which recognizes ICAM-1 (CD54), and G25.2, D12 and SHCL-3, monoclonal antibodies which recognize its receptor LFA-1 (CD11a, CD11b, CD11c), and L130 which recognizes CD18 are known, but there still are some immune reactions which cannot be sufficiently controlled with these monoclonal antibodies.

While molecules which induce intercellular aggregation are cadherins and related adhesion molecules, it has been reported of late that the transmission of signals from CD14, CD18, CD43, CD49d and HLA class II molecules are playing a significant role in the induction of intercellular aggregation. Such induction of intercellular aggregation activates the transmission of information between cells and is a physiological phenomenon for the transfer of external events into the cells.

Moreover, the induction of intercellular aggregation is tantamount to establishing favorable conditions for the proliferation of lymphocytes (T and B cells) and monocytes and, hence, is conducive to activation (potentiation) of the host's immune system.

While the hitherto-known molecules associated with said induction of cell aggregation are cadherins, mentioned above, CD14, CD18, CD43, CD49d, HLA class II and other molecules, these molecules induce intercellular aggregation chiefly in certain groups of immature or mature cells.

The cells of a host body grow into mature cells through several differentiation stages from the beginning of their genesis. AIDS, which is a source of world-wide concern today, is a disease in which mature cells such as peripheral helper T cells and even cells in the monocyte/macrophage series which are considered essential to early defense against infection are destroyed to cause a lowering of autoimmune reaction and, hence, a variety of complicating infectious diseases.

There is accordingly a true need for a molecule which would induce intercellular aggregation and activation of the immune system of a host with compromised immunological potency for the establishment of early defense against infection, for example the aggregation of cells, particularly monocyte series cells, which are in the process of differentiation, other than the mature monocyte series cells in patients with AIDS.

As the result of an intensive research endeavor to solve the above-mentioned problems, the inventors of this invention found that the antibody obtainable by using a lipopolysaccharide-stimulated monocyte/macrophage cell line as the antigen, particularly one of its monoclonal antibodies, remarkably inhibits the interadhesion of cells induced by a differentiation factor and that it suppresses the immune reactions by a new pathway different from any of the pathways of immunosuppression relevant to the known monoclonal antibodies.

It was further discovered that unlike the hither to-known monoclonal antibodies which induce aggregation of certain specific mature cells, another monoclonal antibody, which was also obtained concurrently, induces intercellular aggregation of cells, particularly those in the monocyte series, which have been stimulated by a differentiation factor and are in a certain stage of differentiation in the cell lineage, and that the dynamics of monocyte series cells in said certain stage of differentiation can be investigated by means of this antibody. The inventors found that this antibody can be a very instrumental tool for promoting activation of the immune system through the induction of intercellular aggregation in said monocyte series cells and hence for providing a patient with AIDS who is liable to develop various infectious diseases with the necessary early defense against infection (enhancement of immunopotency). The present invention has been developed on the basis of the above findings.

The antibody of the invention can be obtained by using a lipopolysaccharide-stimulated monocyte/macrophage cell line as the antigen.

An antibody of the invention has activity to inhibit intercellular adhesion of cells (such as cells in the monocyte/macrophage series) stimulated by a differentiation factor (such as lipopolysaccharide, PMA, cytokines, etc.).

Another antibody, particularly a monoclonal antibody, of the invention has activity to induce intercellular aggregation of cells (such as cells in the monocyte/macrophage series) in the course of differentiation under stimulation by differentiation factors (such as lipopolysaccharide, PMA, cytokines, etc.).

The method of this invention for producing an antibody comprises using a lipopolysaccharide-stimulated monocyte/macrophage cell line as the antigen.

The antibodies according to this invention may be polyclonal or monoclonal and can be produced by the procedures well known in the art. However, the monoclonal antibodies are preferred to the polyclonal ones.

The polyclonal antibody can be produced by immunizing an animal, such as a rabbit, with a lipopolysaccharide-stimulated monocyte/macrophage cell line, subjecting the resultant antiserum to the conventional purification procedure such as ammonium sulfate precipitation, centrifugation, dialysis, column chromatography and so on.

As an example of the monocyte/macrophage cell line, the U937 cell can be mentioned.

The lipopolysaccharide-stimulated monocyte/macrophage cell line can be obtained by adding lipopolysaccharide to undifferentiated monocyte/macrophage cells and incubating them. The preferred lipopolysaccharide is the lipopolysaccharide derived from a gram-negative strain of microorganism (e.g. of the genus Salmonella).

On the other hand, the monoclonal antibody (hereinafter referred to sometimes as mAb) can be produced from the antibody-producing cells isolated from a mammalian animal immunized with a lipopolysaccharide-stimulated monocyte/macrophage cell line by subjecting these cells to fusion with appropriate cells derived from an animal and cloning the fused cells capable of producing the object antibody and cultivating the resultant hybridomas.

Thus, to obtain the hybridoma, a mammalian animal is immunized with a lipopolysaccharide-stimulated monocyte/macrophage cell line in the first place. The mammalian animal may be a mouse. As an exemplary practical immunization procedure, the mouse is intraperitoneally or subcutaneously inoculated with the lipopolysaccharide-stimulated monocyte/macrophage cell line. This inoculation using a dose of $10^6$~$10^7$ cells/mouse is repeated a few times at intervals of 1~2 weeks. On day 1~5 after the last immunization, the spleen is isolated for harvesting the antibody-producing cells. Then, as the parent cell for producing a hybridoma by fusion with the above antibody-producing cell, a myeloma or other tumor cell line (such as NS-1) is provided and fused to the antibody-producing cell to obtain a hybridoma.

The medium for use in this preparation of the hybridoma may for example be RPMI1640, Eagle's MEM, Dulbecco's modified MEM or the like, which has been supplemented with 10% calf serum (CS), 5% fetal calf serum (FCS)+5% CS or 10% FCS.

In carrying out the cell fusion, the parent tumor cell, such as myeloma cell, and the splenic cell are provided in a ratio of 1:5 through 1:10. As a fusing agent, polyethylene glycol (PEG) or the like is used. HAT selection of the fused cell strain is carried out by the known method. For the screening of the resultant hybridomas, the culture supernatant is chiefly used and clones of the hybridoma secreting the object immunoglobulin are picked by the known method, such as indirect rosette, enzyme linked immunosorbent assay (ELISA) (Dynatech method), etc. The number of clones was increased gradually and subcloning is performed when $10^5$ cells/ml has been obtained. For testing the singularity of the hybridoma, a 96-well microtiter plate is seeded with about $10^5$ cells/well of normal splenocytes as the feeder layer and, then, with 0.1~0.3 cells/well of the hybridoma and incubated for about 1~2 weeks. The clones that have grown are subjected to screening again. This subcloning is repeated to obtain a singular hybridoma.

Then, for the production of the monoclonal antibody, the hybridoma obtained above is cultured in an incubator (in vitro) or in an animal body (in vivo). The in vivo culture is preferred. In the in vitro culture system, the medium can be an ordinary medium supplemented with CS or FCS as mentioned above. After 3~5 days of culture in such medium, mAb is separated from the culture supernatant. In the in vivo culture system, a mammalian animal such as a mouse is intraperitoneally inoculated with the hybridoma and after 1~2 weeks, the ascites is collected to obtain mAb.

Purification of mAb from such culture supernatant or ascites can be carried out by the known techniques such as ammonium sulfate fractionation, protein A affinity column chromatography and so on.

The properties of such mAb are ascertained from differences in reactivity from the hitherto-known antibodies in several systems.

EXAMPLE 1

Construction of the monoclonal antibody (a) Immunization

The monocyte series cell line (U937 cells) was prepared in 10% FCS-RPMI1640 medium to a concentration of $1\times10^5$ cells/ml.

A 10 ml portion of the suspension was distributed into culture dishes and a lipopolysaccharide (LPS) derived from Salmonella minnesota (No. L-6261, Sigma) was added at a final concentration of 10~20 µg/ml.

After 48 hours' culture in a 5% $CO_2$ incubator, the cells ($5\times10^6$ cells) adhering to the dish were injected into the abdominal cavity of BALB/C mice 3 times at intervals of one week. Thereafter, the cells were intravenously injected once. Both the U937 cell line and NS-1 cell line described below in (c) are frequently used in universities and research institutions and can be easily obtained.

(b) Preparation of splenic cells

On day 3 after the last immunization, the spleen was aseptically isolated and a single cell suspension in RPMI1640 medium was prepared. The erythrocytes were lysed and removed by treatment with Tris-ammonium chloride buffer and the suspension was centrifugally washed 3 times with RPMI1640 medium (1000 rpm, 10 min. each)

(c) Preparation of the parent cell line (P3-NSI/1-Ag4-I;NS-1)

Three (3) days before fusion, NS-1 cells were cultured in 8-azaguanine (100 µM)-15% FCS-RPMI1640 medium to a concentration of $10^5$ cells/ml. The NS-1 cells in the logarithmic phase of growth were recovered from the flask and centrifugally washed 3 times with RPMI1640 medium (1000 rpm, 10 min. each).

(d) Cell fusion

The NS-1 cells, $1\times10^7$, and immunized spleen cells, $1\times10^8$, were mixed in a centrifuge tube (50 ml type) and centrifuged at 1000 rpm for 10 minutes. The supernatant was removed thoroughly with a Pasteur pipet and the cell pellet was loosened up. Then, 0.5 ml of prewarmed PEG solution at 37° C. was added and the reaction was carried out at room temperature for 1 minute. After this 1-minute period, 1 ml of prewarmed RPMI1640 medium at 37° C. was added over a period of about 1 minute.

Thereafter, 1 ml of RPMI1640 medium was added every 30 seconds to finally make a total of 10 ml. The PEG solution was diluted and centrifuged at 1200 rpm (room temperature) for 10 minutes. The supernatant fluid was thoroughly removed.

Then, the pellet was suspended in prewarmed 15% FCS-RPMI1640 medium at 37° C. and the suspension was distributed in 0.1 ml aliquots into a 96-well microtiter plate ($5 \times 10^4$ NS-1 cells/well). After 24 hours, 0.1 ml of prewarmed HAT medium (a medium containing hypoxanthine, aminopterin and thymidine) at 37° C. was added. Thereafter, one-half volume of the HAT medium was changed at intervals of 2~3 days. After 2 weeks, cells began to proliferate, forming colonies, in several wells. When the colonies have occupied not less than ⅓ of the well, the medium was replaced with HT medium (HAT medium from which aminopterin had been omitted). After 1 week of culture in HT medium, the HT medium was gradually replaced with the ordinary medium (15% FCS-RPMI1640 medium). After the cells had proliferated uneventfully, they were transferred to a flask for maintenance.

(e) Cloning

The hybridoma cells were suspended in the ordinary medium and the suspension was distributed into a 96-well microtiter plate at the rate of 0.3 cells/well. Then, using BALB/c mouse thymic cells as the feeder cells, cloning was carried out.

The medium was changed every 3 days. From the clones after about 2 weeks, 3 hybridomas producing the monoclonal antibody against the immunogen were obtained.

The monoclonal antibody obtained from one of these hybridomas which inhibited intercellular adhesion was named NI-58mAb.

In addition, the monoclonal antibody obtained from another hybridoma which induced intercellular aggregation of monocyte series cells in the process of differentiation under stimulation with a differentiation factor was named NI-11mAb.

(f) Preparation of the antibody in ascites and purification

BALB/c mice treated with 0.5 ml of pristane (Sigma) about 1~2 weeks before were inoculated with $10^7$ cells of each hybridoma. The ascites was recovered after 1~2 weeks and purified by using a protein A affinity column.

The characteristics of NI-58mAb of this invention are presented in Examples 2 through 8.

EXAMPLE 2

Determination of the class

The class of NI-58mAb of this invention as obtained in Example 1 was determined by the double immunodiffusion technique. As a result, it was found to be IgG1.

EXAMPLE 3

Identification of the antigen molecule recognized by NI-58mAb

The antigen molecule recognized by NI-58mAb of this invention was explored by Western blotting. The U937 cells were solubilized with lysis buffer (50 mM Tris-HCl, pH 7.4, 150 mM NaCl, 5 mM EDTA, 0.5% NP-40) and the antigen was treated in the presence of 2-mercaptoethanol at 100° C. for 1 minute. A known quantity of the antigen solution was subjected to electrophoresis on 7.5% SDS-PAGE, followed by blotting onto a cellulose membrane. After this blot-transfer, the cellulose membrane was washed with blotting buffer (50 mM Tris-HCl, pH 7.4, 150 m NaCl, 5 m EDTA, 0.25% gelatin, 0.05% Tween 20) and blocked with 5% dry milk. Then, NI-58mAb of this invention in the optimal concentration and peroxidase-labelled goat anti-mouse IgF (ab')$_2$ were permitted to act on the cellulose membrane, followed by a color reaction with a substrate solution. As molecular weight markers, those with molecular weights of 29~205 KD were used. As shown in FIG. 1, the NI-58 antigen recognized by NI-58mAb of this invention was observed as a single band corresponding to a molecular weight of about 65 KD.

EXAMPLE 4

Binding affinities of NI-58mAb for various cells

Various monoclonal antibodies in the optimum concentrations were reacted with various target cells at 4° C. for 1 hour.

The cells of each type were washed with gelatin veronal buffer (GVB) and, then, FITC-labelled goat anti-mouse IgF(ab')$_2$ was added. The reaction was carried out at 4° C. for 20 minutes.

The respective cells were washed again and the cells positive to fluorescent stain were analyzed by flow cytometry.

The results are shown in Table 1.

TABLE 1

| | Binding affinity | | | | | | | | | | | | |
|---|---|---|---|---|---|---|---|---|---|---|---|---|---|
| Antigen | — | CD11a | CD18 | CD29 | CD58 | CD54 | CD44 | CD23 | CD16 | CD11b | CD45RA | HLA(I) | HLA(II) |
| Antibody | NI-58 | G25.2 | L130 | 4B4 | L306.4 | LB-2 | L178 | H107 | Leu11b | Mo-2 | 2H4 | TOK-45 | Sa3 |
| Class | IgG1 | IgG2a | IgG1 | IgG1 | IgG2a | IgG2b | IgG1 | IgG2b | IgM | IgM | IgG1 | IgG2b | IgG3 |
| Mol. wt. of antigen (KD) | 65 | 180/95 | 95 | 135 | 40–65 | 70–80 | 80–95 | 45–50 | 50–60 | 155/95 | 220 | 45 + 12 | 55–65 |
| Target cell | | | | | | | | | | | | | |
| B85 | + | ++ | +++ | −/± | ++ | + | +(P) | +++ | − | − | ++/+++ | +++ | +++ |
| Mann | + | ++ | +++ | −/± | +++ | + | +++ | ++ | − | − | +++ | +++ | +++ |
| Raji | + | − | +/++ | ++ | ++ | +/++ | − | ++ | − | − | +++ | +++ | +++ |
| CEM | + | +++ | +/++ | +++ | ++ | − | +++ | − | − | − | − | +++ | − |
| U937 | ++ | +/++ | +++ | +++ | ++ | + | ++ | + | +/++ | + | +++ | +++ | − |
| THP-1 | + | ++ | +++ | ++ | ++ | + | +++ | nt | − | +/++ | +++ | +++ | ± |
| K562 | − | − | − | ++ | +++ | +/++ | − | − | − | − | +/++ | − | − |
| PBMCs | +++ | ++ | ++ | nt | nt | ± | nt | −/± | nt | nt | nt | +++ | ± |

P: partial positive,
nt: not tested,

TABLE 1-continued

Binding affinity

—: <10%,
±: 10 ~ 20%,
+: 21 ~ 40%,
++: 41 ~ 70%,
+++: >71%
B85, Mann: EBU-transformed B cell line
Raji: Burkitt's lymphoma cell line
CEM: T cell leukemia cell line
U937, THP-1: Myeloid cell line
K562: Erythroid cell line
PBMCs: peripheral blood mononucler cells It is apparent from Table 1 that NI-58mAb of this invention has binding affinities different from the known monoclonal antibodies, particularly the monoclonal antibodies known to inhibit intercellular adhesion (G25.2, MO-2, L130, LB-2) and, therefore, is different from any of these known monoclonal antibodies in regard of the antigen recognized.

In addition, leukemic cells were tested by flow cytometry using NI-58mAb.

The antigen defined by NI-58mAb was expressed on leukemic cells from some patients with acute lymphoblastic leukemia (ALL) (result not shown).

In another experiment, U937 cells were reacted with NI-58mAb and, then, FITC- or PE-labelled CD11a, CD18, CD44, CD54, CD29 and CD11b antibodies were respectively reacted. As a result, all of these antibodies reacted strongly, indicating that NI-58mAb is a new antibody which does not show a cross reaction with any of these antibodies.

EXAMPLE 5

HCA inhibitory effect in LPS-stimulated U937 cells

A 96-well plate was seeded with $1 \times 10^5$ U937 cells and, then, LPS (25 µg/ml) and NI-58mAb of this invention (20 µs/ml) or LB-2 (20 µg/ml, Becton-Dickinson) were added. The plate was incubated for 24 hours and the inhibitory effect of the monoclonal antibody on the intercellular aggregation of LPS-stimulated U937 cells (differentiated to CD14-positive cells) was evaluated under the microscope.

As controls, a no-addition system and an LPS (25 µg/ml) system and, as negative controls, a LPS plus IgG1 antibody system and a LPS plus IgG2b antibody system were used. The results are shown in FIG. 2.

It is apparent from FIG. 2 that NI-58mAb of this invention significantly inhibited the HCA of LPS-stimulated U937 cells and that this inhibitory effect is greater than that of LB-2 at the comparable concentration.

EXAMPLE 6

The change in the amount of expression of the antigen on the surface of U937 cells after LPS stimulation, which is recognized by NI-58mAb of Example 3 (hereinafter referred to as NI-58 antigen), and of CD54 (the antigen for LB-2mAb) was analyzed by flow cytometry.

The results are shown in FIG. 3.

It is apparent from FIG. 3 that whereas CD54 shows a significant increase in expression after LPS stimulation, NI-58 antigen shows no change at all in the amount of expression even after LPS stimulation.

Thus, while the HCA of LPS-stimulated U937 cells can be delegated to the pathway mediated by NI-58 antigen and the pathway mediated by CD54, the pathway mediated by NI-58 antigen, unlike the pathway mediated by CD54, is not affected by the amount of expression of NI-58 antigen after LPS stimulation.

EXAMPLE 7

Inhibitory effect in mixed lymphocyte culture (MLC)

Peripheral blood mononuclear cells (PBMCs) were aseptically separated and suspended in RPMI1640 medium supplemented with 20% normal human serum (a mixture of A, B, AB and O types).

Then, $6 \times 10^4$ responder cells and $6 \times 10^4$ stimulator cells, as well as NI-58mAb (20 µg/ml), were added to a 96-well microtiter plate and cultured in a 5% $CO_2$ incubator at 37° C. for 6 days. In this procedure, the DNA synthesis by stimulator cells was inhibited with 40 µg/ml of mitomycin C.

After 6 days, 1 µCi of $^3$H-thymidine was added to each well and the plate was incubated at 37° C. using a 5% $CO_2$ incubator for 1 day.

After 1 day, the cells were adsorbed on a filter and the intercellular uptake of $^3$H-thymidine during a one-minute period was measured with a liquid scintillation counter (determination of DNA-synthesizing ability). The results are shown in Table 2.

TABLE 2

| Responder cell | Stimulator cell | Uptake of $^3$H-thymidine (cpm) | |
|---|---|---|---|
| | | Without antibody | With NI-58mAb |
| F | — | 714 | 797 |
| F | F | 773 | 574 |
| F | A | 15696 | 3183 |
| A | — | 489 | 286 |
| A | A | 443 | 416 |
| A | F | 6161 | 998 |

It is apparent from Table 2 that since F and A are different individuals and dissimilar in the type of HLA antigen which is a main tissue-compatible complex, the cpm count of the responder T cells shows a high value owing to proliferation (increased DNA-synthesizing ability) when the respective cells are mixed but the cpm count decreases considerably when NI-58mAb of this invention is simultaneously added.

Thus, NI-58mAb appears to inhibit the proliferation of T-cells recognizing the alloantigen, that is to say the mixed lymphocyte culture reaction signifying cellular immunity, through the inhibition of cell recognition based on intercellular adhesion.

EXAMPLE 8

Inhibitory effect on antibody production by pokeweed mitogen (PWM)-stimulated B cells PBMCs were aseptically separated and suspended in 10% FCS-RPMI1640.

The 1×10⁵ PBMCs thus prepared were added to a microtiter plate and, at the same time, PWM was added at a final concentration of (1:50). Then, NI-58mAb was added at a final concentration of 20 µg/ml and the plate was incubated at 37° C. using a 5% $CO_2$ incubator for 7 days.

After the above 7-day period, the cells were recovered and by the reversed plaque method using protein A-bound sheep erythrocytes, the plaques were counted to estimate the antibody production differentiating ability of B cells in the presence of PWM. The results are shown in Table 3.

TABLE 3

| Cultural conditions | IgG-PFC (plaque-forming-cells)/well |
| --- | --- |
| PBMCs | 72 |
| PBMCS + PWM | 1420 |
| PBMCs + PWM + NI-58mAb | 78 |

It is apparent from Table 3 that whereas PWM stimulation of PBMCs results in a significant production of IgG, the simultaneous addition of NI-58mAb of the invention to this system causes a marked decrease in IgG production.

In this system, the B cells among PBMCs are caused by PWM to differentiate and adhere to T lymphocytes, monocyte/macrophage and other cells to become antibody (IgG)-producing cells. Therefore, the observed significant decrease in IgG production indicates that NI-58mAb inhibited the adhesion of B cells to T lymphocytes, monocyte/macrophage series cells and so on.

The characteristics of NI-11mAb of this invention are shown in Examples 9 through 15.

EXAMPLE 9

Determination of the class

The class of NI-11mAb of this invention as obtained in Example 1 was determined by the double immunodiffusion method. It was found to be IgG1.

EXAMPLE 10

Identification of the antigen molecule recognized by NI-11mAb of this invention

The antigen molecule recognized by NI-11mAb of this invention was explored by Western blotting. The U937 cells were solubilized with lysis buffer (50 mM Tris-HCl, pH 7.4, 150 mM NaCl, 5 mM EDTA, 0.5% NP-40). A known quantity of the antigen solution was subjected to electrophoresis on 10% SDS-PAGE, followed by blotting onto a cellulose membrane. After this blotting, the cellulose membrane was washed with blotting buffer (50 mM Tris-HCl, pH 7.4, 150 m NaCl, 5 m EDTA, 0.25% gelatin, 0.05% Tween 20) and blocked with 5% dry milk. Then, NI-11mAb of this invention in the optimal concentration and peroxidase-labelled goat anti-mouse IgF(ab')$_2$ were permitted to act on the cellulose membrane, followed by a color reaction with a substrate solution. As molecular weight markers, those with molecular weights of 29–205 KD were used. As shown in FIG. 4, the NI-11 antigen recognized by NI-11mAb of this invention was observed as a single band corresponding to a molecular weight of about 95–97 KD.

EXAMPLE 11

Binding affinities of NI-11mAb for various cells

Various monoclonal antibodies in the optimum concentrations were reacted with various target cells at 4° C. for 1 hour.

The cells of each type were washed with gelatin veronal buffer (GVB) and FITC-labelled goat anti-mouse IgF (ab')$_2$ was added. The reaction was carried out at 4° C. for 20 minutes.

The respective cells were washed again and the cells positive to fluorescent stain were analyzed by flow cytometry.

The results are shown in Tables 4 and 5.

TABLE 4

| | Binding affinity | | | | | | |
| --- | --- | --- | --- | --- | --- | --- | --- |
| Antigen | — | CD43 | CD11a | CD18 | CD29 | CD58 | CD54 |
| Antibody | NI-11 | DFT1 | G25.2 | L130 | 4B4 | L306.4 | LB-2 |
| Class | IgG1 | IgG1 | IgG2a | IgG1 | IgG1 | IgG2a | IgG2b |
| Mol. wt. of antigen (KD) | 95–97 | 95–130 | 180/95 | 95 | 135 | 40–65 | 70-80 |
| Target cell | | | | | | | |
| B85 | + | ++ | ++ | +++ | −/± | ++ | + |
| Mann | − | +++ | ++ | +++ | −/± | +++ | + |
| Raji | − | − | − | +/++ | ++ | ++ | +/++ |
| CEM | ± | +++ | +++ | +/++ | +++ | ++ | − |
| U937 | ++ | +/++ | +/++ | +++ | +++ | ++ | + |
| THP-1 | −/± | +++ | ++ | +++ | ++ | ++ | + |
| K562 | − | ++/+++ | − | − | ++ | +++ | +/++ |
| PBMCS | ± | nt | ++ | ++ | nt | nt | ± |

P: partial positive, nt: not tested, −: <10%, ±: 10–20%, +: 21–40%, ++: 41–70%, +++: >71%
B85, Mann: EBV-transformed B cell line
U937, THP-1: Myeloid cell line
Raji: Burkitt's lymphoma cell line
K562: Erythroid cell line
CEM: T cell leukemia cell line
PBMCs: peripheral blood mononucler cells

TABLE 5

Binding affinity

| Antigen | CD44 | CD23 | CD16 | CD11b | CD45 RA | HLA (I) | HLA (II) |
|---|---|---|---|---|---|---|---|
| Antibody | L178 | H107 | Leu11b | Mo-1 | 2H4 | TOK-45 | Sa3 |
| Class | IgG1 | IgG2b | IgM | IgM | IgG1 | IgG2b | IgG3 |
| Mol. wt. of antigen (KD) | 80–95 | 45–50 | 50–60 | 155/95 | 220 | 45 + 12 | 55–65 |
| Target cell | | | | | | | |
| B85 | +(P) | +++ | – | – | ++/+++ | +++ | +++ |
| Mann | +++ | ++ | – | – | +++ | +++ | +++ |
| Raji | – | ++ | – | – | +++ | +++ | +++ |
| CEM | +++ | – | – | – | – | +++ | – |
| U937 | ++ | + | +/++ | + | +++ | +++ | – |
| THP-1 | +++ | nt | – | +/++ | +++ | +++ | ± |
| K562 | – | – | – | – | +/++ | – | – |
| PBMCs | nt | –/± | nt | nt | nt | +++ | ± |

P: partial positive, nt: not tested, –: <10%, ±: 10–20%, +: 21–40%, ++: 41–70%, +++: >71%
B85, Mann: EBV-transformed B cell line
U937, THP-1: Myeloid cell line
Raji: Burkitt's lymphoma cell line
K562: Erythroid cell line
CEM: T cell leukemia cell line
PBMCs: peripheral blood mononucler cells It is apparent from Tables 4 and 5 that NI-11mAb of this invention has binding affinities different from the known monoclonal antibodies, particularly the monoclonal antibodies known to induce intercellular aggregation (DFT1, L130) and is, therefore, different from any of these known monoclonal antibodies in regard of the antigen recognized.

EXAMPLE 12

A 96-well plate was seeded with 1×10⁵ U937 cells, either untreated or treated with LPS (10 µg/ml) for 48 hours, followed by addition of NI-11mAb of this invention (15 µg/ml), normal mouse serum (NMS, 15 µg/ml) or TOK-45 (15 µg/ml) which recognizes HLA class I on the surface of U937 cells. Each system was cultured for 6–8 hours, after which it was observed for intercellular aggregation under the microscope. The results are shown in FIGS. 5 and 6.

It is apparent from FIGS. 5 and 6 that NI-11mAb of this invention does not induce HCA of untreated U937 cells [FIG. 5(B)] but induces HCA of LPS-treated U937 cells in a remarkable measure [FIG. 6(b)].

EXAMPLE 13

A 96-well plate was seeded with U937 cells (1×10⁵) treated with LPS (10 µg/ml) for 48 hours followed by addition of NI-11mAb of this invention (15 µg/ml). Then, anti-CD54 antibody (LB-2), anti-CD18 antibody (L130) and anti-CD58 antibody (L306.4) were respectively added at a final concentration of 25 µg/ml. Each system was cultured for 6–8 hours, after which it was observed for intercellular aggregation under the microscope. The results are shown in FIG. 7.

It is apparent from FIG. 7 that the aggregation inducing effect of NI-11mAb of this invention on LPS-stimulated U937 cells is inhibited by LB-2 or L130. It was, therefore, clear that this aggregation inhibitory effect is relevant to the pathway of LFA-1 (CD18)/ICAM-1 (CD54).

EXAMPLE 14

F(ab')² and F(ab') of NI-11mAb were constructed and LPS-stimulated U937 cells were cultured at 37° C. or 4° C. in the presence or absence of each antibody for 4–6 hours. The degrees of aggregation were then evaluated. The degree of aggregation was evaluated by the method of Rothlein and Springer. The results are shown in Table 6.

TABLE 6

| | Concentration (µg/ml) | Degree of aggregation | | |
|---|---|---|---|---|
| | | 37° C. | 4° C. | 4° C.→37° C. |
| NI-11mAb | 10 | 3+ | 0 | 3+ |
| NI-11mAb-F(ab')2 | 10 | 3+ | 0 | 3+ |
| NI-11mAb-F(ab') | 10 | 3+ | 0 | 3+ |
| IgG1 (control) | 10 | 0 | 0 | 0 |
| No addition | — | 0 | 0 | 0 |

The above results suggest that the aggregation induced by NI-11mAb is temperature-dependent and that the molecule controlling the aggregation is integrin.

EXAMPLE 15

A 96-well microtiter plate was seeded with U937 cells (1×10⁵) which had been treated with LPS (10 µg/ml) for 48 hours. Then, NI-11mAb of this invention (15 µg/ml) was added, followed by addition of 2 µM/ml of a C kinase inhibitor, i.e. H-7 or sphingosine. Each system was incubated for 6–8 hours, after which it was observed for intercellular aggregation under the microscope. The results are shown in FIG. 8.

It is apparent from FIG. 8 that the aggregation inducing effect of NI-11mAb of this invention on LPS-stimulated U937 cells is inhibited by C kinase inhibitors. This finding indicated that protein kinase C is associated, in part, with the aggregation inducing effect.

EXAMPLE 16

The reactivity of NI-58mAb and NI-11mAb was analyzed by two-color flow cytometry using the normal adult human peripheral blood mononucler cell as the target cell.

The results are shown in FIGS. 9 and 10.

It is apparent from FIGS. 9 and 10 that whereas NI-58mAb reacts with leukocytes in general, NI-11mAb reacts only with cells in the monocyte series.

Reference Example 1

U937 cells, either untreated or treated with LPS (10 μg/ml) for 48 hours, were stained with the monoclonal antibody (MY-4) against CD14 antigen and FITC-antimouse IgF (ab')2 and the expression of CD14 antigen was analyzed by the FACS method. The results are shown in FIG. 11.

As apparent from FIG. 11, the expression of CD14 antigen was found with the progress of time in the LPS-treated U937 cells (24.3% after 48 hours; 32.2% after 72 hours), indicating that U937 cells are caused by LPS to progress to a certain stage of differentiation of the cell lineage.

Reference Example 2

The cytokines-producing potentials of untreated U937 cells and U937 cells treated with LPS (10 μg/ml) for 48 hours were analyzed by RIA or EIA. The results are shown in Table 7.

TABLE 7

|  | Cytokine | | |
| --- | --- | --- | --- |
|  | IL-6 (pg/ml) | TNF-α (pg/ml) | IL-1β (U/ml) |
| Medium only | <4.0 | <5.0 | 95.0 |
| Untreated U937 cells | <4.0 | <5.0 | 95.0 |
| LPS-treated U937 cells | 327.0 | <5.0 | 108.0 |

It is apparent from Table 7 that LPS-treated U937 cells release a large amount of IL-6 into the culture supernatant. Thus, LPS-treated U937 cells have been transformed into IL-6-producing cells.

Reference Example 3

The dynamics of CD11a, CD11b, CD11c, CD18 and CD54 on the surface of untreated U937 cells and of U937 cells treated with LPS (10 μg/ml) for 48 hours were analyzed by the FACS method.

The results are shown in FIG. 12.

It is apparent from FIG. 12 that LPS-treated U937 cells show a marked increase in CD54.

A moderate increase was also found in CD11b. It is clear that LPS treatment is followed by a remarkable increase in the expression of CD54 on the U937 cell surface.

Reference Example 4

The phase contrast electron microscopic findings of untreated U937 cells and of U937 cells treated with LPS (10 μg/ml) for 48 hours are reproduced in FIG. 13.

It is apparent from FIG. 13 that compared with untreated U937 cells, LPS-treated U937 cells had a remarkable process formation.

Effects of the invention

Among the antibodies of this invention which are obtainable by using a lipopolysaccharide-stimulated monocyte/macrophage cell line as the antigen, NI-58mAb significantly inhibits intercellular adhesion of cells stimulated by a differentiation factor.

Moreover, this NI-58mAb has potent inhibitory activity against intercellular adhesion through a completely different mechanism from that of the monoclonal antibodies so far known to inhibit intercellular adhesion, thus enabling us to suppress the immune reaction which could not be sufficiently inhibited.

Therefore, clinically the antibody is expected to be instrumental for the control of graft rejection following organ transplantation, artificial modulation of adhesion molecules in autoimmune diseases, modulation of adhesion molecules on the surface of endothelial cells in circulatory organ diseases, particularly associated with atherosclerosis, and suppression of the proliferation and metastasis of cancer cells with which adhesion molecules are associated.

Referring to fundamental or preclinical applications, the antibody of the invention is considered to be of value for the elucidation of the intercellular transmission of information associated with the intercellular adhesion of monocyte/macrophage cells, study of the adhesiveness of monocytes/macrophages to endothelial cells in inflammation, and clarification of the suppression of immune responses of T cells, B cells and monocytes/macrophages as induced by various extraneous antigens.

On the other hand, among the antigens of the invention which are obtainable by using a lipopolysaccharide-stimulated monocyte/macrophage cell line as the antigen, NI-11mAb acts in a completely different mechanism from that of the monoclonal antibodies so far known to induce intercellular aggregation of certain mature cells to induce intercellular aggregation of cells, particularly monocyte series cells, which are in the process of differentiation due to stimulation by differentiation factors.

Furthermore, NI-11mAb was found to have an ability to induce marked morphological changes (differentiation to tissue macrophages) in PMA-pretreated U937 cells.

Therefore, the antibody not only facilitates the activation of monocyte cell groups which is of importance for early defense against infection but, through administration to a living body, offers the opportunity to promote the intercellular transmission of monocyte series cells in the process of differentiation, which exist particularly in cases of AIDS accompanied by the destruction of peripheral mature helper T cells and monocyte/macrophage cells and complicated by various infections due to compromised autoimmunity.

Through this intercellular transmission, the antibody promotes the activation of the immune system of the living body and may prove to provide for a very instrumental immunotherapy in this disease for which no effective therapeutics have been available to this day. Furthermore, since the antibody of this invention acts specifically on monocyte series cells which are associated with early defense against infection, it can be used in the exploration into the dynamics of monocyte cell groups which are in the stage of differentiation in patients with AIDS, thus being of value in clinical diagnosis.

Figure 1:
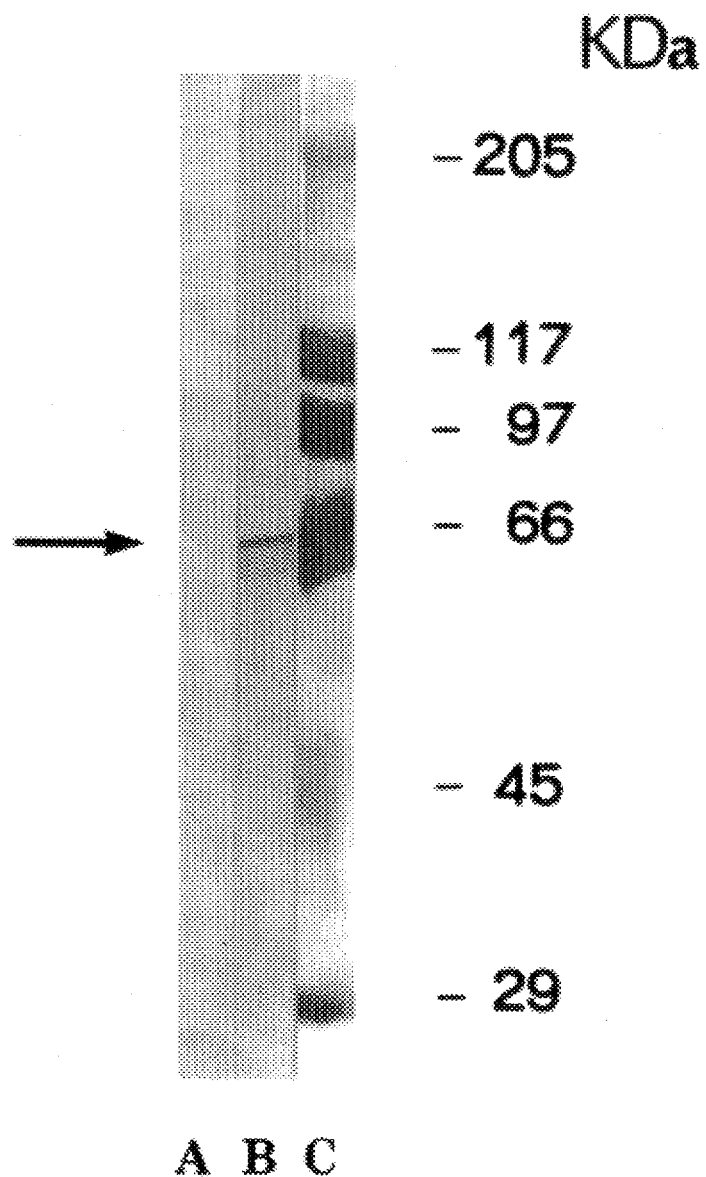
FIG. 1
Figure 2A:
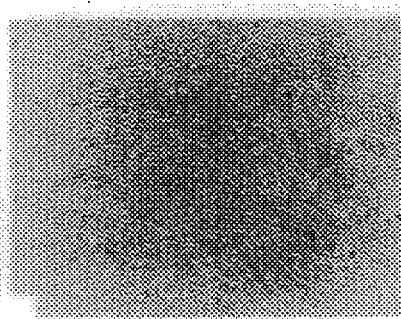
Figure 2D:
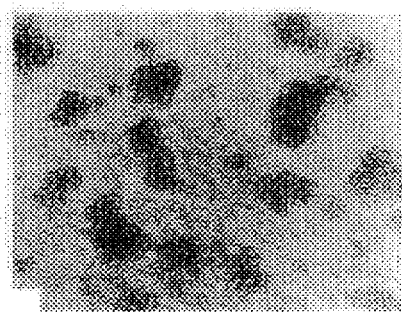
Figure 2B:
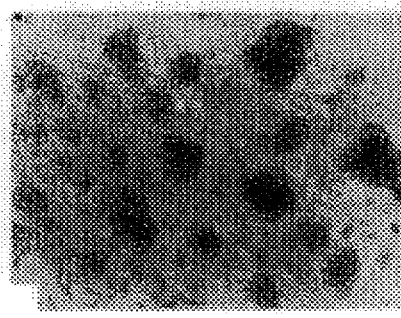
Figure 2E:
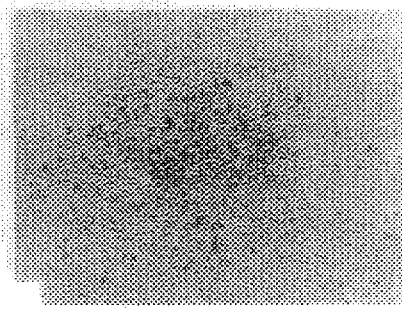
Figure 2C:
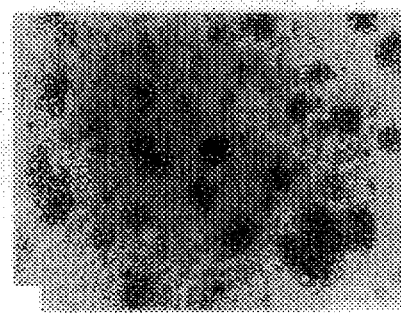
Figure 2F:
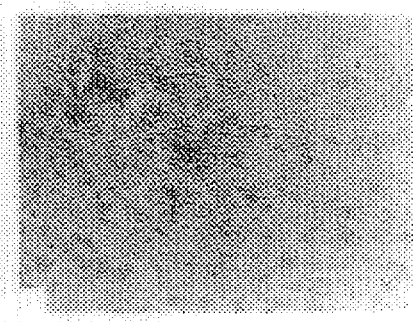
Figure 3A:
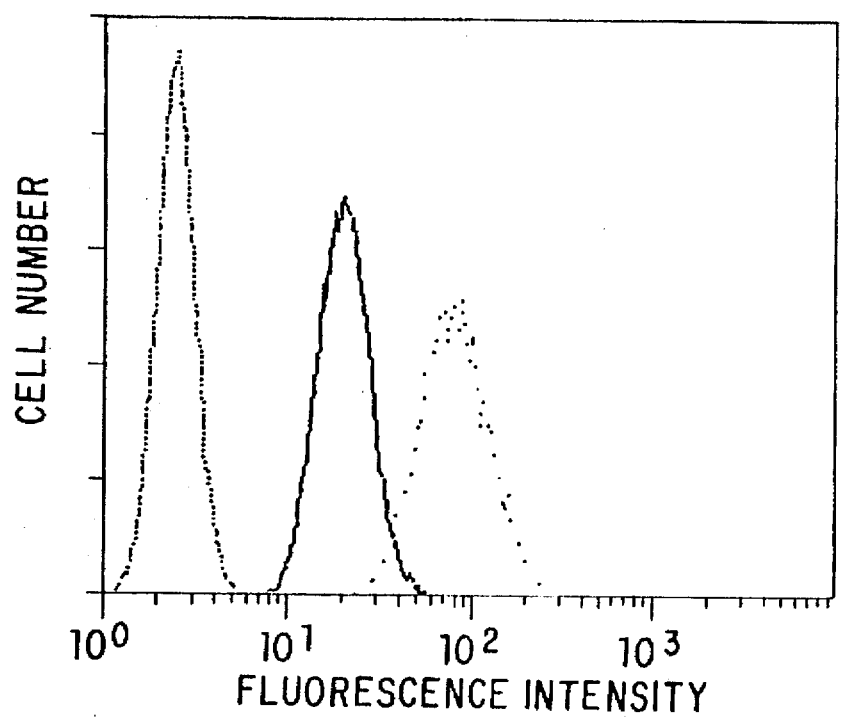
Figure 3B:
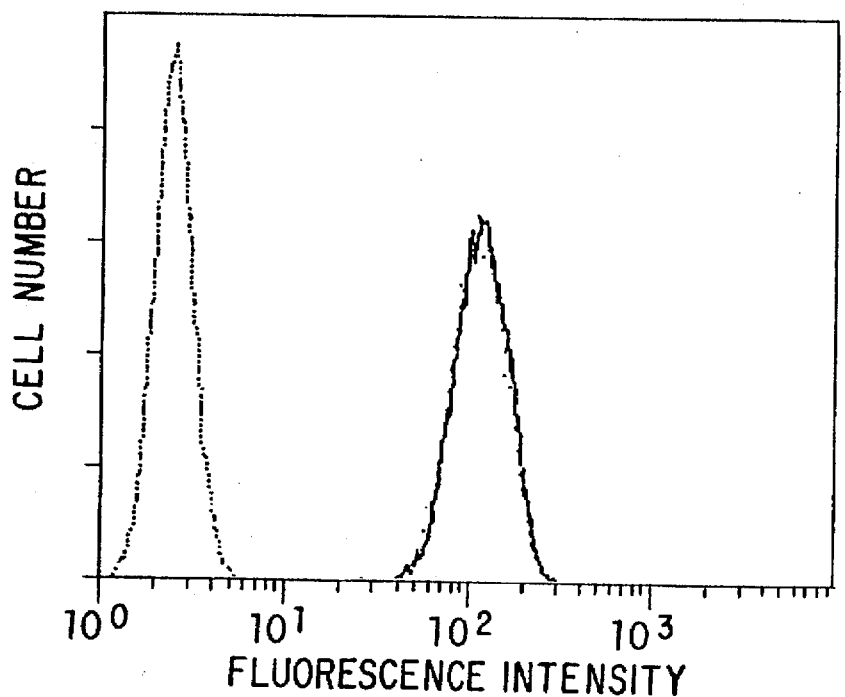
Figure 4:
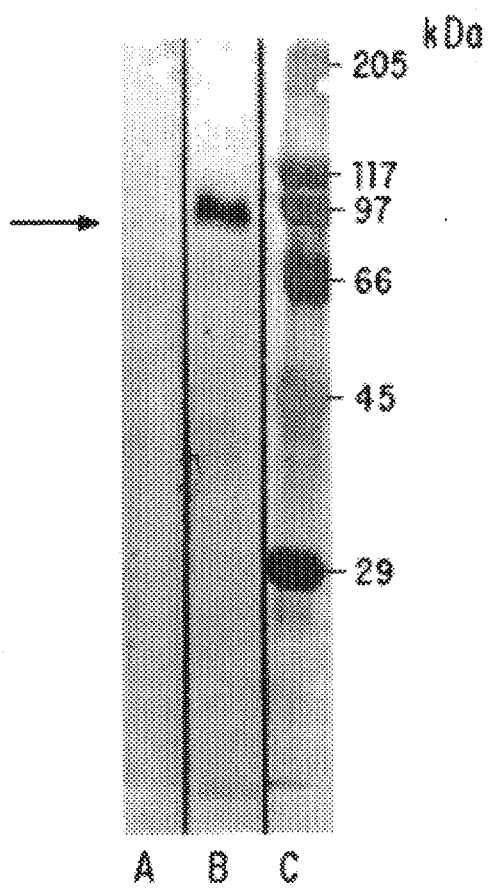
Figure 5A:
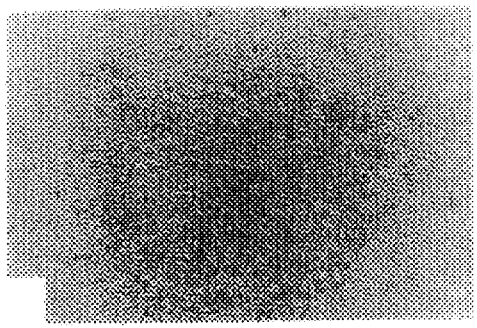
Figure 5C:
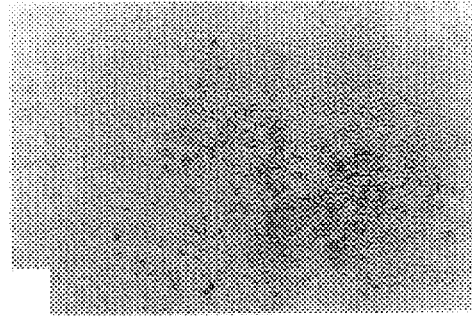
Figure 5B:
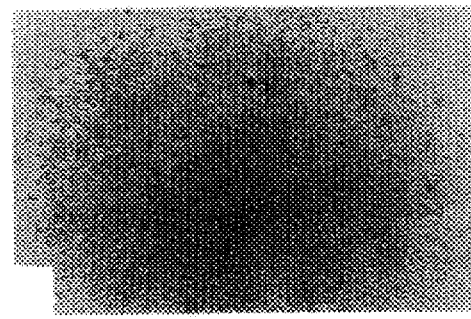
Figure 5D:
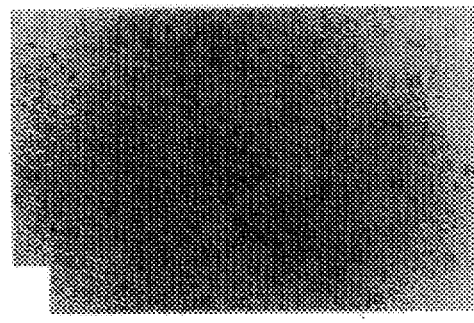
Figure 6A:
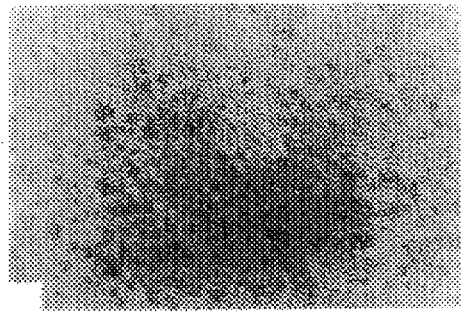
Figure 6C:
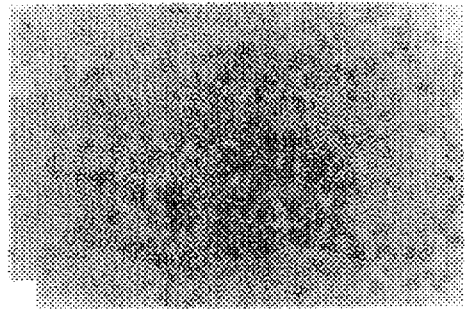
Figure 6B:
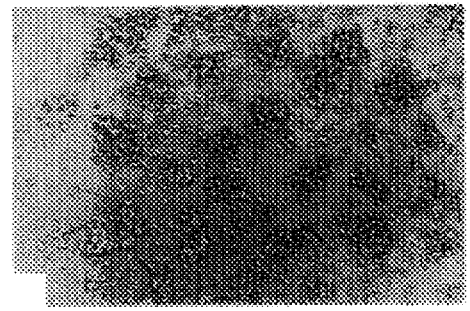
Figure 6D:
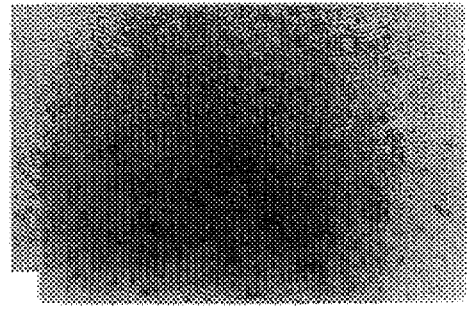
Figure 7E:
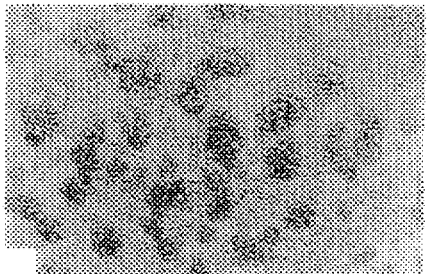
Figure 7G:
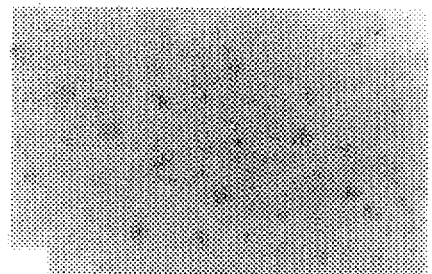
Figure 7F:
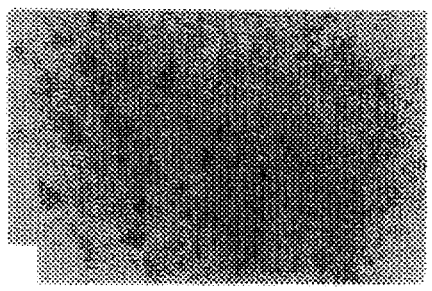
Figure 7H:
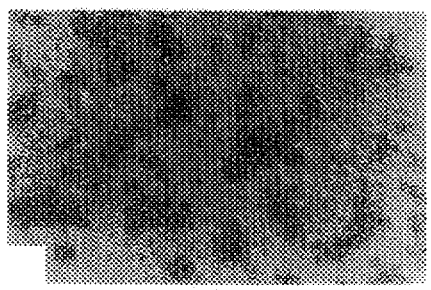
Figure 8I:
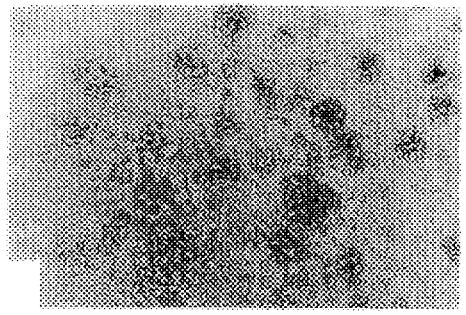
Figure 8K:
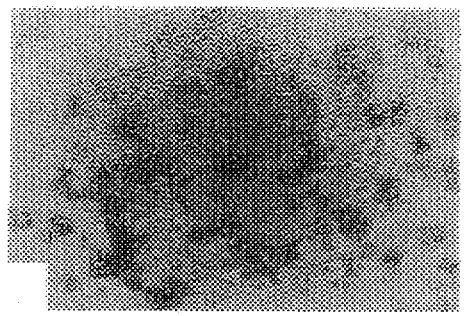
Figure 8J:
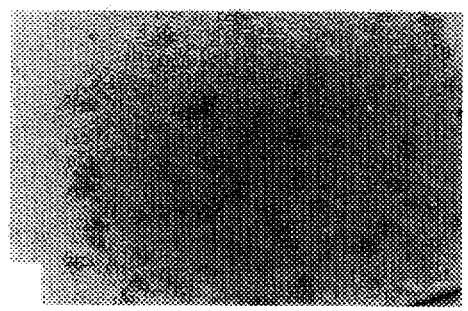
Figure 9A:
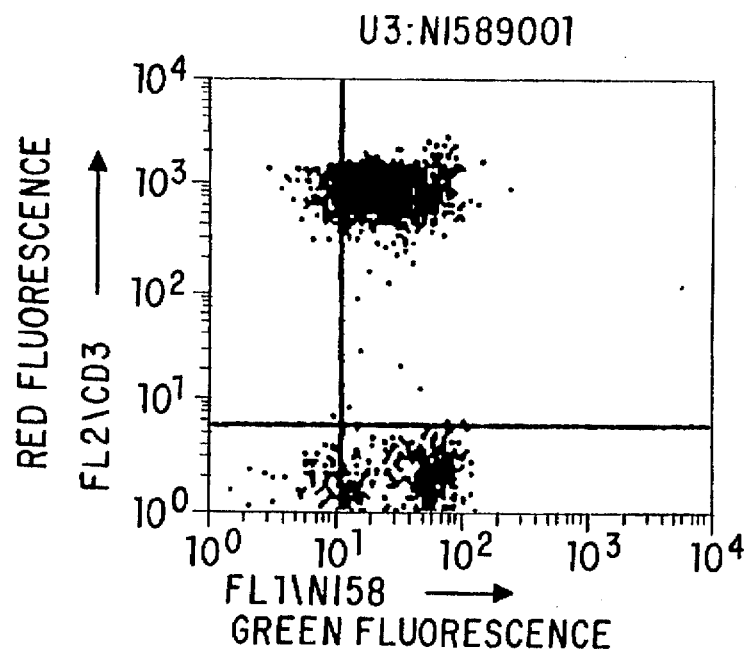
Figure 9B:
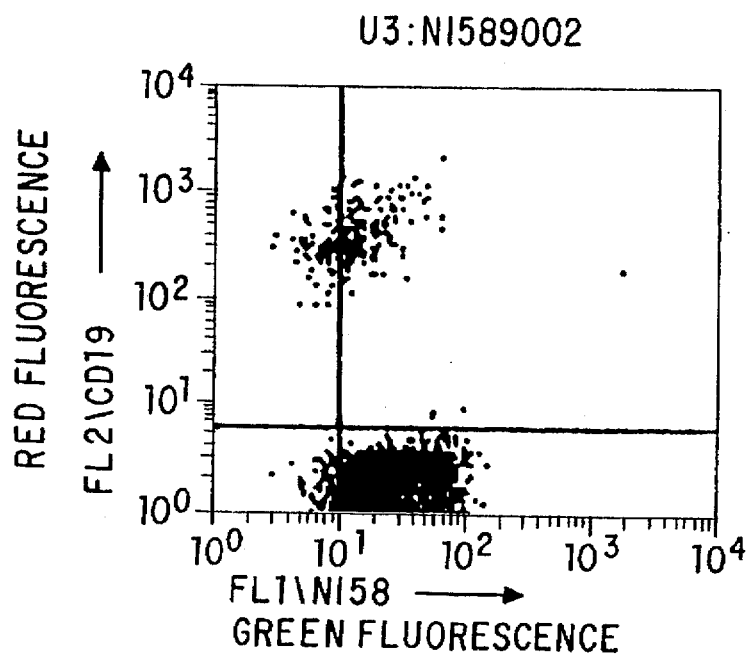
Figure 9C:
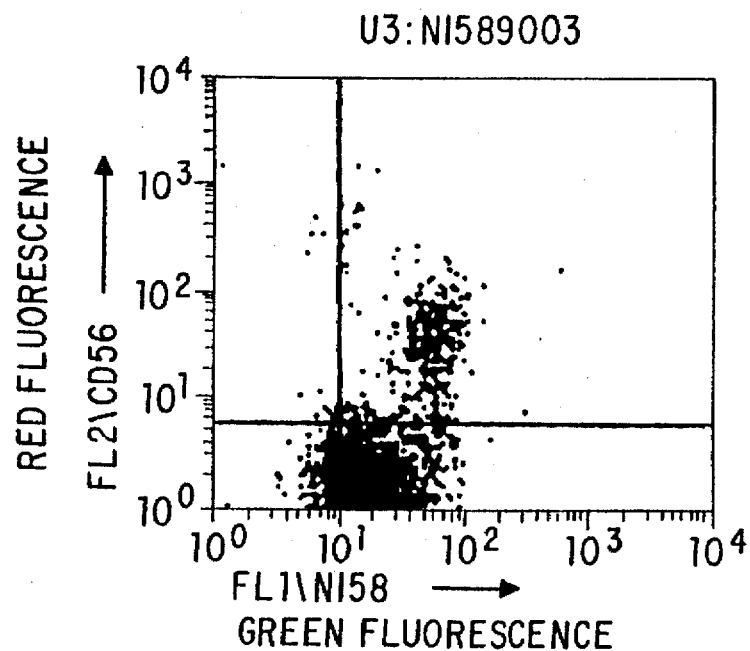
Figure 9D:
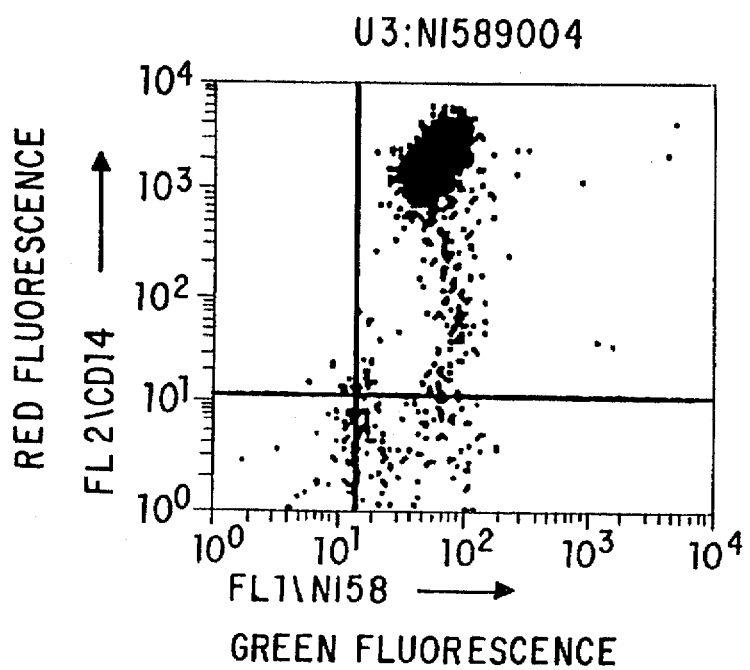
Figure 9E:
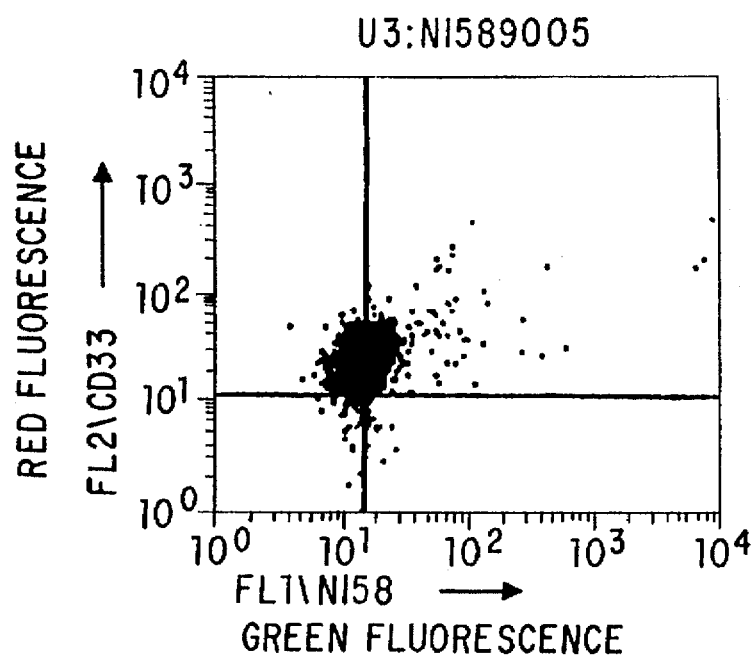
Figure 10A:
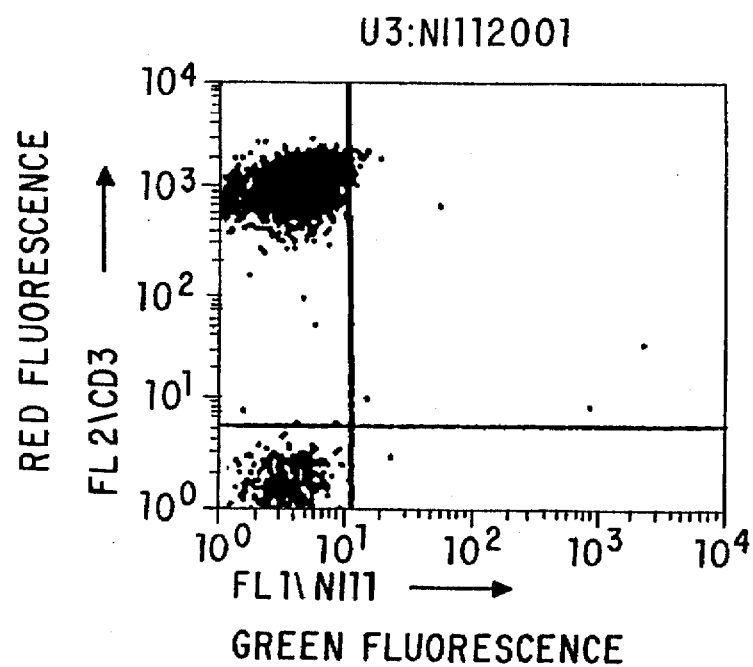
Figure 10B:
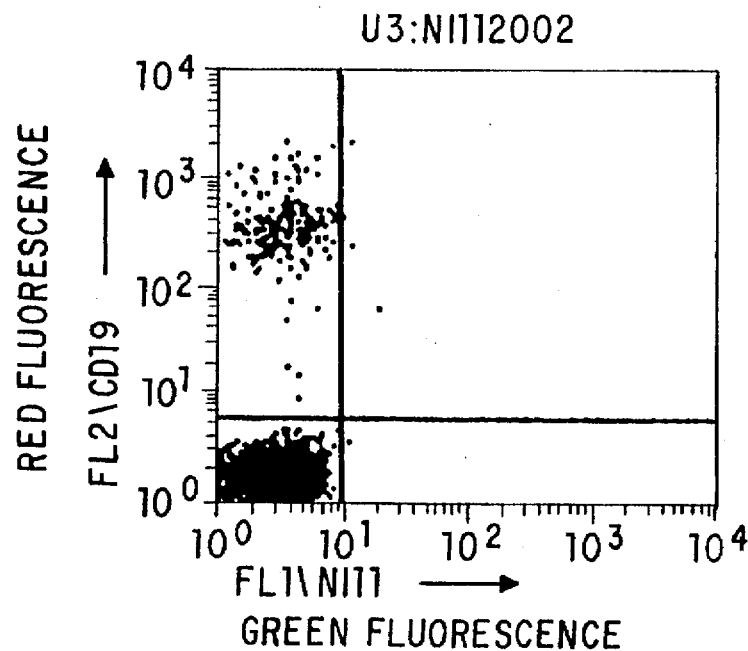
Figure 10C:
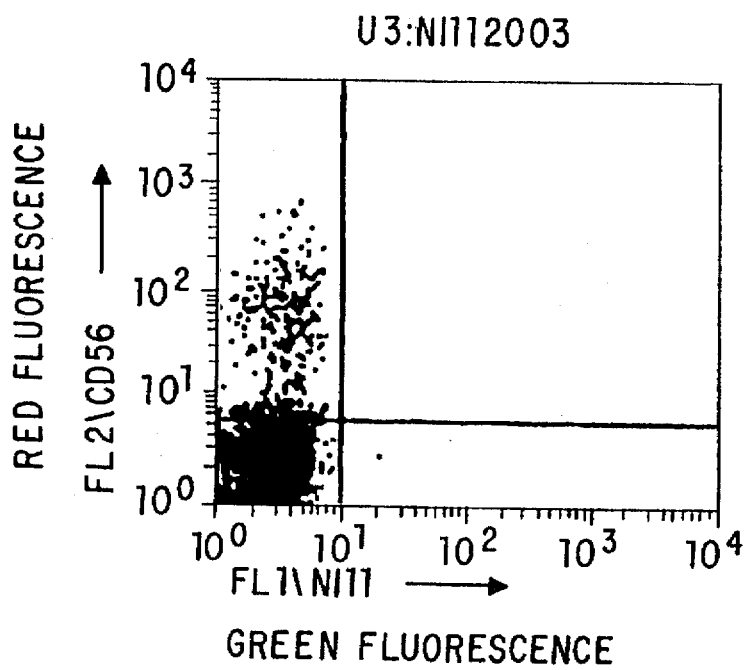
Figure 10D:
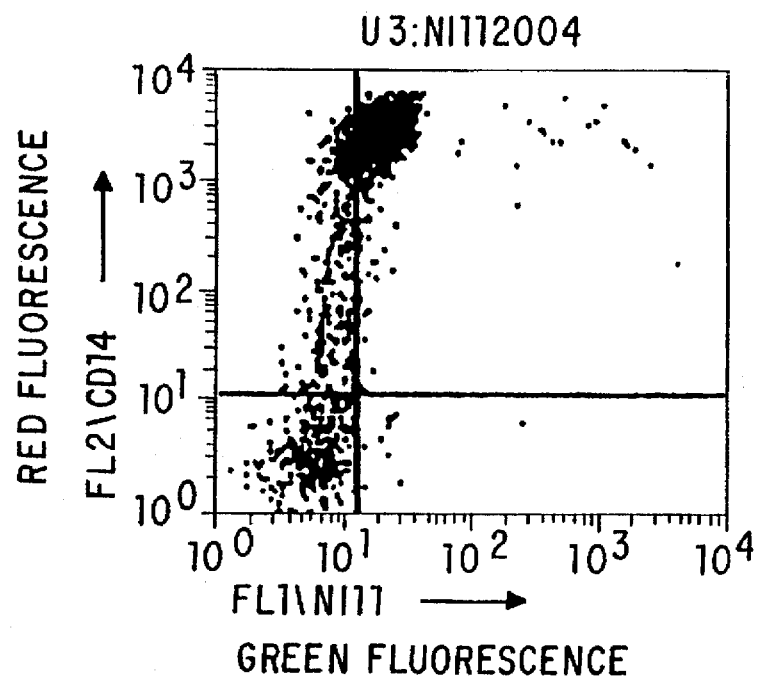
Figure 10E:
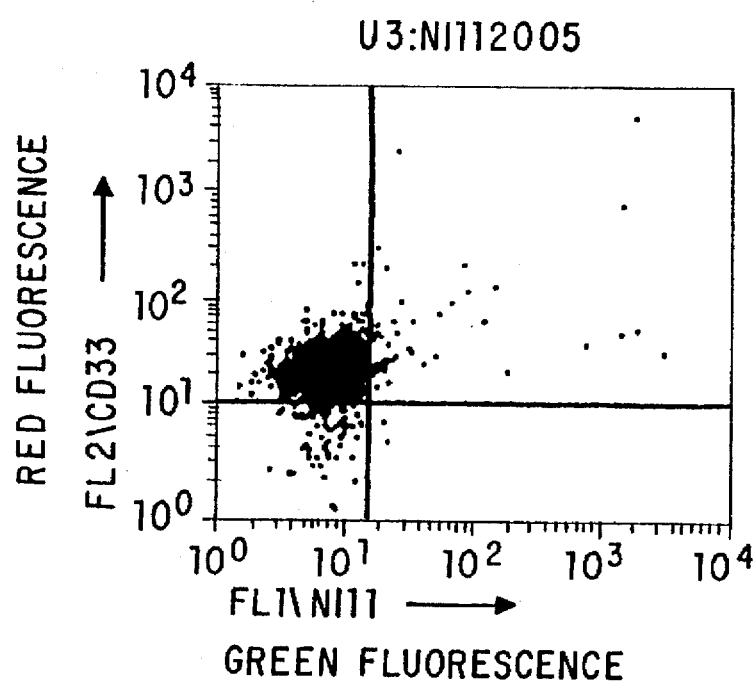
Figure 13A:
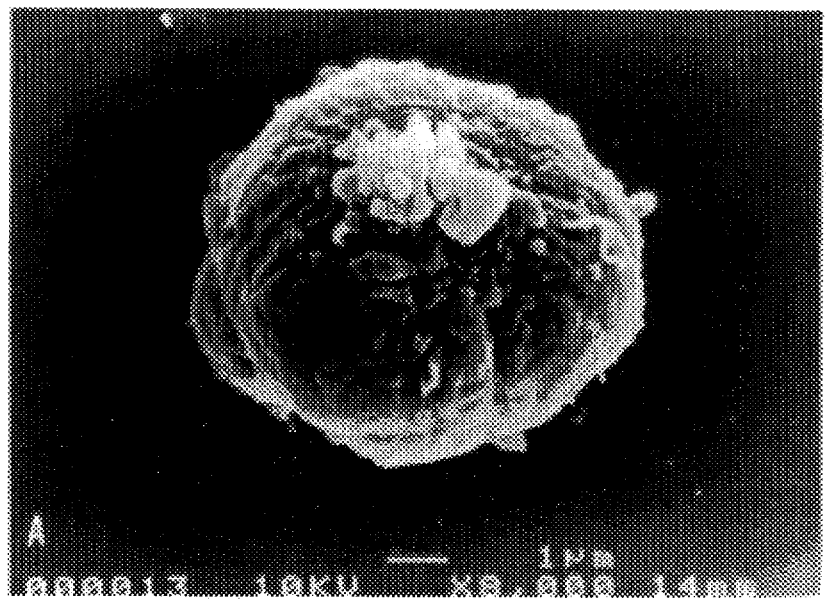
Figure 13B:
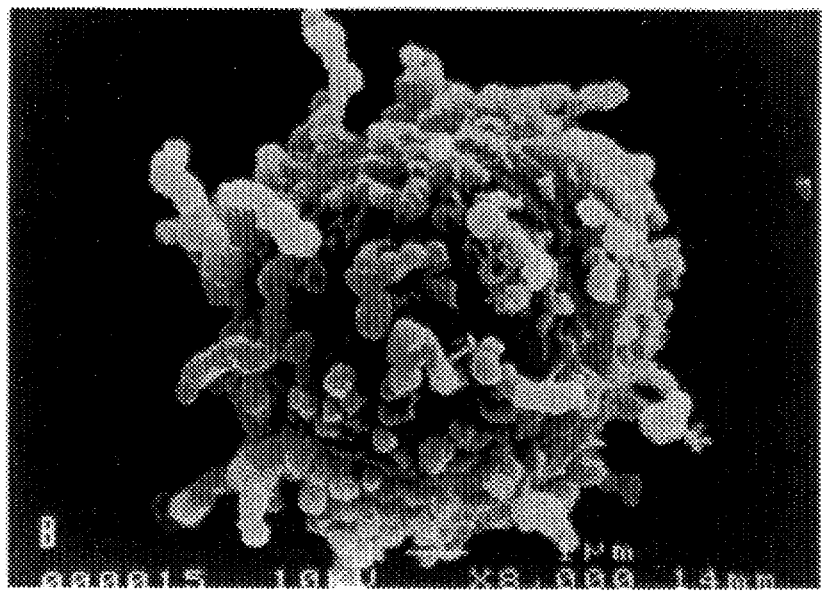

An electrophoregram showing the antigen molecule recognized by the monoclonal antibody (NI-58mAb) of this invention.

The arrowmark in B indicates the position of the antigen molecule recognized by the monoclonal antibody of this invention.

The figures at right represent the molecular weights (KD) of the respective molecular weight markers.

FIGS. 2A–2F

Photographs showing HCA inhibition in the LPS-stimulated U937 cell.

2A No addition
2B LPS (25 μg/ml) added
2C LPS+IgG1 (20 μg/ml) added
2D LPS+IgG2b (20 μg/ml) added 2E LPS+NI-58mAB (20 µg/ml) added
2F LPS+LB-2mAb (20 µg/ml) added

FIGS. 3A–3B

Photographs showing changes in CD54 and NI-58 antigens on the surface of LPS-stimulated U937 cells.

3A The unbroken line represents unstimulated CD54, the sparse dotted line represents LPS-stimulated CD54, and the dense dotted line represents unstimulated negative control.

3B The unbroken line represents unstimulated NI-58 antigen, the sparse dotted line (mostly over-lapping with the unbroken line) represents LPS-stimulated NI-58 antigen, and the dense dotted line represents unstimulated negative control.

FIG. 4

An electrophoregram showing the antigen molecule recognized by the monoclonal antibody (NI-11mAb) of this invention.

The arrowmark in B indicates the position of the antigen molecule recognized by the monoclonal antibody of this invention.

The figures at right represent the molecular weights (KD) of the respective molecular weight markers.

FIG. 5A–5D

Photographs showing the effect of NI-11mAb on untreated U937 cells.

5A No addition
5B NI-11mAb (15 µg/ml) added
5C NMS (15 µg/ml) added
5D TOK-45 (15 µg/ml) added

FIG. 6A–6D

Photographs showing the effect of NI-11mAb on. LPS (10 µg/ml)-treated U937 cells 6A No addition
6B NI-11mAb (15 µg/ml) added
6C NMS (15 µg/ml) added
6D TOK-45 (15 µg/ml) added

FIG. 7E–7H

Photographs showing the HCA inhibitory effects of anti-CD54 antibody and anti-CD18 antibody on NI-11mAb-induced LPS-treated U937 cells.

7E NI-11mAb (15 µg/ml) added
7F NI-11mAb+LB-2 (25 µg/ml) added
7G NI-11mAB+L130 (25 µg/ml) added
7H NI-11mAb+L306.4 (25 µg/ml) added

FIGS. 8I–8K

Photographs showing the partial HCA inhibitory effects of C kinase inhibitors on NI-11mAb-induced LPS-treated U937 cells.

8I NI-11mAb (15 µg/ml) added
8J NI-11mAb+H-7 (2 µM/ml) added
8K NI-11mAB+sphingosine (2 µM/ml) added

FIG. 9

A two-color flow cytometric chart showing the reactivity of NI-58mAb.

FIG. 10

A two-color flow cytometric chart showing the reactivity of NI-11mAb.

FIG. 11

Photographs showing the expression of CD14 antigen by untreated and LPS-treated U937 cells.

FIGS. 12A–12E

Photographs showing the dynamics of CD11a, CD11b, CD11c, CD18 and CD54 on the surface of U937 cells after LPS stimulation.

12A CD11a 12B CD11b 12C CD11c 12D CD18 12E CD54

Dense dotted line: negative control

Unbroken line: not LPS-stimulated

Sparse dotted line: LPS (10 µg/ml)-stimulated

FIGS. 13A–13B

Phase contrast electron microphotographs of the untreated U937 cell and LPS (10 µg/ml, 48 hours)-treated U937 cells.

13A: untreated U937 cells
13B: LPS-treated U937 cells

What is claimed is:

1. An antibody produced by immunizing with a lipopolysaccharide-stimulated monocyte/macrophage cell line as the antigen, wherein said lipopolysaccharide is obtained from a gram-negative strain of microorganism and said antibody inhibits intercellular adhesion of monocyte/macrophage cells stimulated by a differentiation factor.

2. The antibody of claim 1, wherein said differentiation factor is a lipopolysaccharide.

3. The antibody of claim 1 wherein said monocyte/macrophage cells are U937 cells.

4. The antibody of claim 1 which is a monoclonal antibody.

5. The antibody of claim 1 which belongs to the IgG1 class.

6. The antibody of claim 1 which is specifically capable of recognizing a molecule with a molecular weight of about 65 KD.

7. An antibody produced by immunizing with a lipopolysaccharide-stimulated monocyte/macrophage cell line as the antigen, wherein said lipopolysaccharide is obtained from a gram-negative strain of microorganism and said antibody induces intercellular aggregation of monocyte/macrophage cells in the process of differentiation under stimulation by a differentiation factor.

8. The antibody of claim 7 wherein said differentiation factor is a lipopolysaccharide.

9. The antibody of claim 7 wherein said monocyte/macrophage cells are U937 cells.

10. The antibody of claim 7 which is a monoclonal antibody.

11. The antibody of claim 7 which belongs to the IgG1 class.

12. The antibody of claim 7 which is specifically capable of recognizing a molecule having a molecular weight in the range of 95–97 KD.

13. A method of producing an antibody, which inhibits intercellular adhesion of monocyte/macrophage cells stimulated by a differentiation factor which comprises using a lipopolysaccharide-stimulated monocyte/macrophage cell line as the antigen, wherein said lipopolysaccharide is obtained from a gram-negative strain of microorganism.

14. The method of producing an antibody as claimed in claim 13 wherein said antibody is a monoclonal antibody.

15. A method of producing an antibody which induces intercellular aggregation of monocyte/macrophage cells in the process of differentiation under stimulation by a differentiation factor, which comprises using a lipopolysaccharide-stimulated monocyte/macrophage cell line as the antigen, wherein said lipopolysaccharide is obtained from a gram-negative strain of microorganism.

* * * * *